Figure 1:
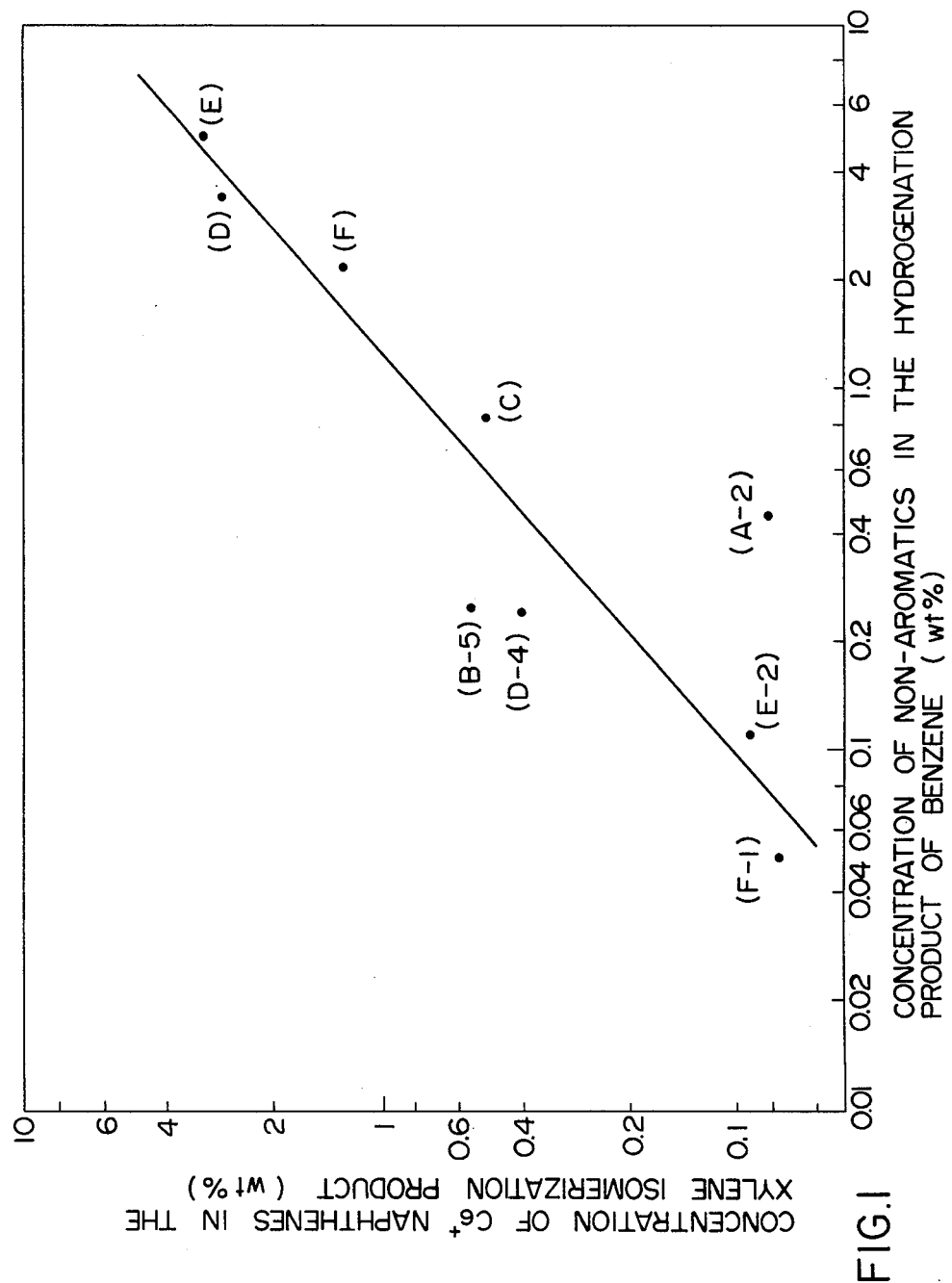

United States Patent [19]

Onodera et al.

[11] Patent Number: 4,485,185
[45] Date of Patent: Nov. 27, 1984

[54] CATALYST COMPOSITION

[75] Inventors: Tamio Onodera; Tokuji Sakai; Yasuo Yamasaki; Koji Sumitani, all of Matsuyama, Japan

[73] Assignee: Teijin Petrochemical Industries, Ltd., Tokyo, Japan

[21] Appl. No.: 532,305

[22] Filed: Sep. 15, 1983

Related U.S. Application Data

[63] Continuation of Ser. No. 307,435, Oct. 1, 1981, abandoned, which is a continuation-in-part of Ser. No. 133,793, Mar. 25, 1980, Pat. No. 4,331,822.

[30] Foreign Application Priority Data

Mar. 29, 1979 [JP] Japan .................................. 54-36269

[51] Int. Cl.$^3$ ............................................ B01J 29/32
[52] U.S. Cl. ......................................... 502/71; 502/77
[58] Field of Search ................. 252/455 Z; 502/71, 77

[56] References Cited

U.S. PATENT DOCUMENTS

| | | | |
|---|---|---|---|
| 2,983,670 | 5/1961 | Seubold, Jr. | 252/455 Z |
| 3,894,104 | 7/1975 | Chang et al. | 208/141 X |
| 3,925,254 | 12/1975 | Oishi | 252/455 Z |
| 3,945,913 | 3/1976 | Brennan et al. | 208/137 |
| 3,948,758 | 4/1976 | Bonacci et al. | 208/111 X |
| 3,960,978 | 1/1976 | Givens et al. | 585/531 |
| 4,116,870 | 9/1978 | Weisang et al. | 585/482 |
| 4,120,910 | 10/1978 | Chu | 208/120 X |
| 4,152,363 | 5/1979 | Tabak et al. | 585/481 |
| 4,157,293 | 6/1979 | Plank et al. | 208/135 |
| 4,176,050 | 11/1979 | Chen et al. | 252/455 Z |
| 4,278,565 | 7/1981 | Chen et al. | 585/640 X |

Primary Examiner—Carl F. Dees
Attorney, Agent, or Firm—Sherman & Shalloway

[57] ABSTRACT

A catalyst composition comprising (i) a crystalline aluminosilicate selected from the group consisting of zeolite ZSM-5, zeolite ZSM-11, zeolite ZSM-12, zeolite ZSM-35 and zeolite ZSM-38 and having a silica/alumina mole ratio of 20 to 1,000; and (ii) at least two metals which are (a) platinum and (b) at least one other metal selected from the group consisting of titanium, chromium, zinc, gallium, germanium, strontium, yttrium, zirconium, molybdenum, palladium, tin, barium, cerium, tungsten, osmium, lead, cadmium, mercury, indium, lanthanum and beryllium. This catalyst composition is useful particularly for the isomerization of aromatic hydrocarbons and reforming of naphtha.

20 Claims, 1 Drawing Figure

CATALYST COMPOSITION

CROSS-REFERENCE TO RELATED APPLICATION

This application is a continuation of application Ser. No. 307,435 filed Oct. 1, 1981, now abandoned, which in turn is a continuation-in-part application of application Ser. No. 133,793 filed Mar. 25, 1980 now U.S. Pat. No. 4,331,822.

BACKGROUND OF THE INVENTION

1. Field of the Invention

This invention relates to an improved catalyst composition. More specifically, it pertains to an improved platinum-zeolite type catalyst composition having a long life, excellent heat resistance and high activity and selectivity for conversion of aromatic hydrocarbons, for example the isomerization of xylenes and reforming of naphtha.

2. Description of the Prior Art

Zeolite, or crystalline aluminosilicate, generally has high activity in the conversion reactions of hydrocarbons, such as cracking, hydrocracking, reforming, isomerization and alkylation. Many catalysts compositions based on zeolite have therefore been proposed to date. Isomerization of xylenes is one typical reaction which is carried out in the presence of a zeolite-base catalyst.

Isomerization of xylenes is industrially performed by the steps, in suitable combinations, of isomerizing an aromatic hydrocarbon stock containing mainly xylene isomers, separating a specified xylene isomer, normally p-xylene, from the resulting isomerization reaction mixture, and recycling the mixture left after the separation. It is industrially significant in this case, for an increased efficiency of the isomerization reaction and a reduced cost of production, to adjust the composition of the xylene isomers in the isomerization reaction product as closely as possible to the thermodynamic equilibrium composition, and to inhibit side-reactions such as the decomposition of xylenes (particularly, the hydrogenation of the benzene ring) and disproportionation reaction.

Many methods for isomerizing xylenes have been suggested in the past, and many of them involve the use of a crystalline aluminosilicate zeolite-containing catalyst. Extensive work has been done to improve and develop catalysts and improve the isomerization reaction conditions in regard to the aforesaid prior methods, and a number of suggestions have been made as a result of such work. In particular, much research efforts have been concentrated on methods involving changing the shape or structure of the zeolite catalyst itself; methods involving modifying the zeolite catalyst by subjecting it to a physical treatment, for example heat-treatment, and methods involving chemically modifying the zeolite catalyst by adding various ingredients. For example, there have been suggested a method in which Y-type zeolite is treated with super heated steam to improve its activity and stability (see U.S. Pat. No. 3,887,630), and a method in which $MoO_3$ is supported on offretite to improve its activity to decompose ethylbenzene (see U.S. Pat. No. 3,848,009).

None of the prior suggested catalysts for isomerization of xylenes completely meets two contradictory requirements (a) and (b) below. (a) To have superior activity on the isomerization of xylenes, and (b) to greatly reduce undesirable side-reactions (such as the hydrogenation of the benzene ring, hydrogenolysis, demethylation, and particularly disproportionation and transalkylation).

In the case of isomerizing xylene isomers containing ethylbenzene, it is desirable to deethylate ethylbenzene in addition to the isomerization reaction of the xylenes, and some methods for this purpose have been suggested, for example as seen in U.S. Pat. Nos. 4,098,836, 4,163,028, and 4,152,363.

In the previously suggested methods, however, undesirable side-reactions such as hydrogenation of the benzene ring, disproportionation of xylenes and transalkylation of xylenes and ethylbenzene take place in addition to the isomerization of xylenes and the deethylation of ethylbenzene, and a loss of xylenes cannot be avoided.

For example, the aforesaid three U.S. Patents disclose a method for isomerizing xylene isomers containing ethylbenzene using ZSM-series zeolites modified with a metal of Group VIII of the Periodic Table such as platinum or nickel. With ZSM-series zeolite catalysts modified with nickel (with a nickel content of at least 2% by weight), demethylation of xylene is promoted under severe reaction conditions in which the conversion of ethylbenzene is high, and the loss of xylene increases. It has therefore been considered to be advantageous in industrial operation to use a platinum-group metal which induces little demethylation. ZSM-series zeolites modified with platinum have superior activity of isomerizing xylenes and superior ability to deethylate ethylbenzene selectively. However, platinum itself has a high ability to hydrogenate the benzene ring, and the hydrogenation occurs markedly as the temperature decreases owing to thermodynamic equilibrium. Consequently the amount of naphthenes formed increases and a loss of xylene increases. Accordingly, ZSM-type zeolite catalysts modified with platinum need to be used in industrial applications at temperatures of as high as more than 800° F. (427° C.). The temperature required for the isomerization reaction is affected by the space velocity, but generally, temperatures of about 300° to 340° C. are sufficient. At high temperatures, the isomerization is not improved, but rather undesirable side-reactions such as disproportionation and transalkylation are promoted to cause an increased loss of xylenes.

In order to avoid such undesirable reactions as much as possible, a method has also been suggested in which the space velocity based on the zeolite catalyst is increased to increase the optimum isomerization temperature to a level higher than in ordinary methods and therefore to promote deethylation while inhibiting a loss of xylenes attributed to disproportionation, etc. (see U.S. Pat. No. 4,152,363). With this method, however, it is difficult to maintain the isomerization at a high level, and the degradation of the catalyst increases because the temperature and the space velocity are high.

SUMMARY OF THE INVENTION

It is a primary object of this invention to provide an improved platinum-zeolite catalyst which is significantly free from the defects of the platinum-containing ZSM-series zeolite catalysts, such as their ability to catalyze the hydrogenation of the benzene ring, the disproportionation of xylene and the transalkylation reaction of xylene and ethylbenzene, while retaining their superior ability to isomerize xylenes and to selectively deethylate ethylbenzene.

Other objects and advantages will become apparent from the following description.

According to this invention, there is provided, a catalyst composition comprising (i) a crystalline aluminosilicate selected from the group consisting of zeolite ZSM-5, zeolite ZSM-11, zeolite ZSM-12, zeolite ZSM-35 and ZSM-38 and having a silica/alumina mole ratio of 20 to 1,000, and (ii) at least two metals which are
(a) platinum, and
(b) at least one other metal selected from the group consisting of titanium, chromium, zinc, gallium, germanium, strontium, yttrium, zirconium, molybdenum, palladium, tin, barium, cerium, tungsten, osmium, lead, cadmium, mercury, indium, lanthanum and beryllium.

The crystalline aluminosilicate (to be sometimes referred to as zeolite) forming the base of the catalyst of this invention contains mainly hydrogen or a hydrogen precursor such as an ammonium ion at a cation site and has a silica/alumina mole ratio of from 20 to 1000, more preferably from 30 to 200. In other words, a so-called high-silica zeolite having a high content of silica relative to alumina is used as a base of the catalyst. Many zeolites having a high silica content relative to alumina have been suggested heretofore, and a zeolite having an extremely high silica content represented by a silica/alumina mole ratio of as high as 2,000 is also known. In the present invention, there is conveniently used a low zeolite which has a relatively low silica/alumina ratio and therefore, has a relatively high acid activity attributed to the alumina component.

Crystalline aluminosilicates, or zeolites, having a silica/alumina mole ratio within the above-specified range include ZSM series zeolites developed by Mobil Oil Corporation. The present invention is particularly characterized by the fact that zeolites ZSM-5 (see U.S. Pat. No. 3,702,886) ZSM-11 (U.S. Pat. No. 3,709,979), ZSM-12 (see U.S. Pat. No. 3,832,449), ZSM-35 (see U.S. Pat. No. 4,016,245) and ZSM-38 (see U.S. Pat. No. 4,046,859) which exhibit especially good isomerizing activity on aromatic hydrocarbons are used as bases of the catalyst composition of the invention.

These zeolites are generally available in a form containing an alkali metal ion or an alkaline earth metal ion at the cation site. In the present invention, these zeolites are converted to H-form zeolites, and used in a form containing mainly a hydrogen ion or a hydrogen-precursor ion such as an ammonium ion at the cation site. The content of the hydrogen ion or the hydrogen-precursor ion is not strictly limited. It is very desirable that generally at least 50%, preferably at least 75%, of the entire cation sites present in the zeolite be occupied by the hydrogen ion or hydrogen-precursor ion. Accordingly, unless otherwise indicated, "zeolite" used in the present application denotes H-form zeolite.

It has been found that the use of ZSM-5 zeolite as a base of catalyst produces the best effect. Thus, according to the most preferred embodiment of this invention, ZSM-5 zeolite is used as a base of the catalyst composition.

According to this invention, there is used as a main ingredient of the catalyst composition a product obtained by modifying the aforesaid zeolite with at least two metals which are (a) platinum [to be referred to as metal (a)], and (b) at least one metal selected from the group consisting of titanium, chromium, zinc, gallium, germanium, strontium, yttrium, zirconium, molybdenum, palladium, tin, barium, cerium, tungsten, osmium, lead, cadmium, mercury, indium, lanthanum and beryllium [to be referred to as metal (b)].

Investigations of the present inventors have led to the surprising discovery that zeolite catalysts modified with only platinum have superior ability to isomerize xylenes but at the same time, catalyze undesirable reactions such as the hydrogenation of the benzene ring and the demethylation of xylenes and these catalytic reactions cause an increased loss of xylenes in the isomerization of xylenes, but that when both platinum [metal (a)] and metal (b) are incorporated together into zeolite, the resulting catalyst retains the high ability to isomerize xylenes which the zeolite having only metal (a) incorporated therein possesses, and its undesirable catalytic reaction on such reactions as the hydrogenation of the benzene ring and the demethylation of xylenes can be effectively inhibited.

Titanium, tin, barium, indium and lanthanum are preferred as metal (b) because they have the great ability to inhibit the side-reactions. Titanium and tin are most preferred.

The term "modified with the metal (a) and (b)", as used herein, means that the metals (a) and (b) are ion-exchanged at the cation site of zeolite and/or the metals (a) and (b) or compounds containing them are physically deposited on the surface of zeolite.

Zeolites modified with metals (a) and (b) may be prepared by methods generally known in the modification of zeolites with metals. Modification with metal (a) and modifications with metal (b) may be performed separately in the desired order, or simultaneously. In a preferred embodiment, modification with metal (b) is carried out after the modification with metal (a).

To facilitate understanding, typical examples of the modifying method are described below in detail.

Commercially available zeolites generally have alkali metal ions or alkaline earth metal ions such as Na, K or Ca substituted at the cation site thereof. Hence, the alkali metal or alkaline earth metal ion is exchanged with hydrogen or an ammonium ion. This exchange may be performed simultaneously with, or prior to, the modification with metal (a).

One method comprises dipping a zeolite having its cation site substituted with an alkali metal or alkaline earth metal ion in an aqueous solution containing a metal (a) ion and an ammonium ion to give a zeolite product which is modified with the metal (a) and in which a greater portion of the cation site is of the ammonium ion form. Calcination of the resulting ammonium ion-form zeolite modified with the metal (a) at a temperature of about 200° to 600° C. gives a hydrogen ion-form zeolite modified with the metal (a).

Another method comprises treating a zeolite having its cation site substituted with an alkali metal or alkaline earth metal ion with an inorganic or organic acid such as hydrochloric acid, sulfuric acid, nitric acid, acetic acid or oxalic acid to convert a greater portion of the cation site to a hydrogen ion form, and exchanging the hydrogen ion with a metal (a) ion or depositing the metal (a) on the resulting zeolite.

Still another method comprises treating a zeolite having its cation side substituted by an alkali metal or alkaline earth metal ion with an aqueous solution of a water-soluble ammonium compound to form a zeolite having a greater portion of its cation site substituted with an ammonium ion, which zeolite is then optionally converted to an H-form zeolite by calcination at a temperature of, for example, about 200° to about 600° C., and finally exchanging the ammonium ion or hydrogen ion with a metal (a) ion, or depositing the metal (a) on the ammonium ion-type or hydrogen ion-type zeolite. In this method, substitution by an ammonium ion can be easily carried out by contacting the zeolite with an aqueous solution of a water-soluble ammonium compound such as ammonium chloride or ammonium nitrate in a concentration of 5 to 20% by weight.

Ion exchange of zeolite with a metal (a) and/or deposition of the metal (a) on the zeolite can be performed by techniques known to be used in subjecting ordinary zeolites to ion exchange with metal (a) or in depositing noble metal (a) on such zeolites.

For example, a zeolite to be treated is contacted with an aqueous or non-aqueous medium containing a compound of the desired noble metal dissolved therein. Such noble metal compounds include the halides, oxides, sulfides, oxy acid salts, and complexes. When zeolite is modified with metal (a) (platinum), the zeolite may be impregnated with an aqueous solution of a water-soluble platinum compound (such as $H_2PtCl_6$, or $PtCl_2$) and then water is evaporated off to deposit platinum on the zeolite. Or the zeolite may be dipped in an aqueous solution of a platinum compound having ion exchange ability such as a platinum-amine complex [e.g., $Pt(NH_3)_4Cl_2$], and then subjected to filtration, followed by sufficient washing. As a result, the zeolite is ion-exchanged with a platinum cation.

Prior to the modification treatment with metal (a), zeolite may be heated for 1 to 50 hours in an oxygen atmosphere such as air or an inert gaseous atmosphere such as nitrogen at a temperature of 100° to 700° C., preferably 200° to 600° C. This generally gives better catalysts.

The zeolite modified with metal (a) may be heated in an oxygen-containing atmosphere such as air or an inert gaseous atmosphere such as nitrogen at a temperature of 100° to 700° C., preferably 200° to 600° C., for about 1 to about 5 hours. This heat-treatment is preferred in this invention.

The zeolite modified with metal (a) in the above manner is then modified with metal (b). Modification with metal (b) may be carried out by the same method and under the same conditions as in the modification with metal (a) described hereinabove. Accordingly, the modification with metal (b) is not particularly different from usually known methods for preparing modified zeolites using various methods.

Examples of the various metal compounds used to perform modification with metal (b) are given below. These examples are merely illustrative, and it should be understood that any water-soluble or solvent-soluble compounds of the respective metals can be equally used even if they are not specifically exemplified herein.

(1) Titanium Compounds

Titanium fluoride, chloride, bromide, iodide sulfate and nitrate, ammonium hexafluorotitanate, ammonium pentafluoroperoxotitanate, ammonium hexachlorotitanate, diethyl ammonium hexachlorotitanate and hexabromotitanate, and bis(acetonitrile)tetrachlorotitanium.

(2) Chromium Compounds

Chromous chloride, chromous sulfate, chromous acetate, chromic chloride, chromic nitrate, chromic sulfate, hexamine chromic compound, dichromic acid, and ammonium dichromate.

(3) Germanium Compounds

Germanium tetrachloride, germanium dichloride, and germanium tetraalkyl.

(4) Molybdenum compounds

Molybdic acid, ammonium molybdate, and molybdenum pentachloride.

(5) Palladium Compounds

Palladium chloride, palladium sulfate, palladium nitrate, and tetraammine palladium chloride.

(6) Tin Compounds

Stannous chloride, tin tetrachloride, chlorostannous acid, tin tetraalkyl, ammonium hexachlorostannate, and tetraethylammonium trichlorostannate.

(7) Barium Compounds

Barium fluoride, chloride, chlorate perchlorate, bromide, bromate, iodide, thiosulfate, dithionate, sulfate, nitrate, phosphate, carbonate, thiocyanate, metalsilicate, acetate, hydroxide, formate, hydrogen-phosphate, lactate, oxalate, nitrite and sulfite.

(10) Tungsten Compounds

Tungstic acid, and ammonium paratungstate.

(11) Osmium Compounds

Osmic acid, and osmium tetrachloride.

(12) Lead Compounds

Lead acetate, lead nitrate, lead chlorate, and lead tetraalkyl.

(13) Cadmium Compounds

Cadmium chloride, perchlorate, bromide, iodide, sulfate, nitrate, cyanide, thiocyanate, carbonate, formate, hydroxide and sulfide, tris(ethylenediamine) cadmium nitrate, and dichloro(ethylenediamine)cadmium.

(14) Indium Compounds

Indium fluoride, chloride, bromide, iodide, perchlorate, sulfate and nitrate, ammonium hexafluoroindate, and ammonium aquapentachloroindate.

(15) Other Metal Compounds

Compounds of strontium, beryllium, gallium, yttrium, zirconium, zinc, cerium, lanthanum, and mercury, such as the corresponding fluorides, chlorides, bromides, iodides, perchlorates, cyanides, sulfates, nitrates, nitrites, sulfides, acetates, oxalates, formates, lactates, citrates, carbonates, phosphates, thiocyanates, thiosulfates, hydroxides, oxides, chlorates, chlorites, iodate, and various kinds of complex compounds thereof.

The contents of the metals (a) and (b) in the zeolite modified with the metals (a) and (b) in accordance with this invention can be varied depending upon the type of the metal used. The content of metal (a) is generally 0.001 to 2% by weight, preferably 0.005 to 1.5% by weight, more preferably 0.01 to 1% by weight, based on the weight of the crystalline aluminosilicate. The contents of the metal (b) is such that the atomic ratio of metal (a) to metal (b) is generally from 1:0.01 to 1:10, preferably from 1:0.5 to 1:5, more preferably from 1:0.1 to 1:3.

The catalyst of this invention so prepared contains the metal (a) in the form of a cation and/or oxide and the metal (b) in the form of a cation and/or oxide depending upon the type of the metal, before it is reduced prior to use in the reaction. When the catalyst is reduced prior to use in the reaction, the metal (a) is converted to an elemental form, and the metal (b), to an element, oxide or cataion, or mixtures thereof.

The zeolite catalyst of the invention can be prepared either as a fine powder or an various other desired shapes such as pellets or tablets molded in a customary manner. A shaped article of the modified zeolite can be obtained in a customary manner by mixing the modified zeolite with a synthetic or natural refractory inorganic oxide usually employed as a binder for zeolite-type catalysts, such as silica, alumina, silica-alumina, kaolin or silica-magnesia, shaping the mixture into the desired configuration, and then calcining the shaped article. Advantageously, the amount of the modified zeolite as an active catalyst ingredient in the shaped article is generally 1 to 99% by weight, preferably 10 to 90% by weight, based on the weight of the shaped article.

In use, the catalyst composed of zeolite modified with the metals (a) and (b) prepared in the above-mentioned manner is treated in a reducing atmosphere such as a hydrogen gas at a temperature of 200° to 600° C., preferably 250° to 550° C. This reducing treatment is usually carried out after the catalyst has been filled in a reactor.

The catalyst composition of this invention prepared in the above manner can be characterized by various excellent properties described below.

(1) Cyclohexane/n-hexane sorption ratio

The cyclohexane/n-hexane sorption ratio is a parameter which represents a measure of the pore dimension of the zeolite catalyst, and denotes the ratio of the weight of cyclohexane adsorbed per unit weight of the zeolite catalyst at a constant temperature and pressure to the weight of n-hexane adsorbed per unit weight of the zeolite catalyst at the constant temperature and pressure. That this ratio is low means that molecules having a large cross section such as cyclohexane, have difficulty in diffusing through the pores of the zeolite. This brings about an advantage of increasing selectivity in a catalyzed reaction. The amount of cyclohexane or n-hexane adsorbed per unit weight of the zeolite can be measured by weighing a fixed amount of the zeolite catalyst calcined at 450° C. for 8 hours in an electric furnace, then maintaining the weighed zeolite for 6 hours in an atmosphere of a saturated gas of cyclohexane or n-hexane at 25° C. and 120±20 mmHg, further weighing the zeolite catalyst after it has been maintained at 25° C. and 120±20 mmHg in the absence of cyclohexane or n-hexane, and calculating the weight difference of the catalyst before and after adsorption. A more specific method of measurement is described in detail in Example 3 given hereinbelow.

The catalyst zeolite provided by this invention generally has a cyclohexane/n-hexane sorption ratio of not more than 0.95, preferably not more than 0.8, more preferably not more than 0.6. The lower limit to the sorption ratio varies depending upon the type of the starting zeolite used in the preparation of the catalyst and the types and amounts of the metal (a) and/or the metal (b) used in the catalyst preparation. Generally, it is about 0.05, desirably 0.1 or more.

(2) Activity Index

The "activity index", as used in the present application, denotes the relative cracking activity of the catalyst composition of the invention in comparison with a conventional highly active silica-alumina cracking catalyst. It is measured by the following method.

A catalyst sample molded to a size of 10–20 mesh is calcined in air at 450° C. for 8 hours. 1.5 ml of the calcined catalyst is packed into a quartz reactor tube. Nitrogen gas saturated with n-hexane at 25° C. is fed into the catalyst bed kept at constant temperature (200° C.) at a rate of 10 ml/min at atmospheric pressure. The conversion of n-hexane is measured, and the reaction rate constant at that temperature is calculated. The activity index (A.I.) is computed from the following equation.

$$A.I. = \frac{\text{Reaction rate constant of the catalyst at 200° C.}}{\text{Reaction rate constant of the silica/alumina catalyst at 200° C.}}$$

The method for measuring A.I. is described in detail in Example 2 given hereinbelow.

The catalyst zeolite of the invention generally has an A.I. of not less than 100, preferably not less than 1,000, when it is measured by the above method.

(3) Hydrogenation Index

The term "hydrogenation index" (to be abbreviated H.I.), used in the present application, denotes the total weight percent of $C_6$ naphthenes which are formed when a 1:1 (mole) gaseous mixture of benzene and hydrogen is passed over the zeolite catalyst of the invention under fixed reaction conditions (200° C., 1 atm.) at a weight hourly space velocity (WSHV) of 8 $hr^{-1}$. That the H.I. is high means that the catalyst has high hydrogenating activity on the benzene ring. The high H.I. leads to an increase in the loss of aromatic hydrocarbons in the reactions.

H.I. is measured by the following method.

A sample zeolite catalyst molded into pellets having a size of 10 to 20 mesh is calcined at 450° C. for 8 hours in an electric furnace, and a fixed amount of the calcined catalyst sample is weighed. It is then packed into a fixed bed reactor vessel. A 1:1 (mole) mixture of benzene and hydrogen is fed into the catalyst bed under fixed reaction conditions (200° C., 1 atm.) at a WHSV of 8 $hr^{-1}$. After a lapse of two hours from the initiation of feeding, the total amount (weight percent) of $C_6$ naphthenes is measured, and defined as H.I.

The catalyst composition of this invention generally has an H.I. of not more than 6%, preferably not more than 2%, more preferably not more than 0.5% when it is measured by the above method. One advantage of the invention is that when the catalyst composition of the invention is used in the isomerization of xylene, the loss of xylenes is very small.

(4) Catalyst life

Since the catalyst composition of the invention has a very low H.I. value as stated above, hydrogenation and hydrogenolysis of the benzene ring do not appreciably take place. This offers the advantage that deposition of coke on the catalyst surface is very much reduced. Accordingly, the catalyst of the invention permits operation for a longer period of time than conventional catalysts, and enables the reaction to be carried out at lower temperatures and pressures.

(5) Heat stability

Since deposition of coke on the surface of the catalyst composition of this invention is reduced as stated above, heat generation during the regeneration of the catalyst is small, and therefore, the platinum site does not easily undergo damage during the regeneration. Then, after the operation the performance of the catalyst composition is stable.

Thus, the catalyst composition provided by this invention can be used, for example, as in isomerization catalyst in isomerizing an aromatic hydrocarbon stock containing predominantly xylene isomers not attaining a thermodynamic equilibrium composition at an elevated temperature in the vapor phase in the presence of hydrogen.

The aromatic hydrocarbon stock to be used in the isomerization of xylenes prodominantly contains xylene isomers which has not attained a thermodynamic equilibrium composition. As is well known, xylene contains three isomers, ortho-, meta- and para-isomers. It is known that when a mixture in an arbitrary ratio of the three isomers is subjected to an isomerization reaction, the reaction reaches an equilibrium when the ratio among the three isomers attains a certain specific value, and apparently no further advance of the isomerization is noted. The composition of the xylene isomers at such an equilibrium state is called the "thermodynamic equilibrium composition". The thermodynamic equilibrium composition varies slightly depending upon temperature, and for example, the xylene isomers have the following thermodynamic equilibrium composition at the following temperature.

| [I] Mixture consisting only of three xylene isomers (at 427° C.):- | |
|---|---|
| p-Xylene | 23.4% by weight |
| m-xylene | 52.1% by weight |
| o-Xylene | 24.5% by weight |
| [II] Mixture of xylene isomers and ethylbenzene (at 427° C.):- | |
| Ethylbenzene | 8.3% by weight |
| p-Xylene | 21.5% by weight |
| m-Xylene | 47.8% by weight |
| o-Xylene | 22.4% by weight |
| | 100% by weight in total |

In the present specification, the term "xylene isomeric mixture not attaining a thermodynamic equilibrium composition" denotes a xylene isomers mixture in which the concentration of at least one of the three xylene isomers falls outside the thermodynamic equilibrium composition.

The aromatic hydrocarbon stock to be used as a starting material in the process of this invention may consist only of the xylene isomers, or may be a mixture of the xylene isomers with another aromatic hydrocarbon such as ethylbenzene, benzene, toluene, ethyltoluene, trimethylbenzene, diethylbenzene, ethylxylene, and tetramethylbenzene. In the latter case, the xylene isomeric mixture is present desirably in an amount of generally at least 30% by weight, preferably at least 50% by weight, based on the weight of the aromatic hydrocarbon stock.

$C_8$ aromatic hydrocarbon fractions obtained by reforming, thermal cracking or hydrocracking of naphtha can be used especially advantageously as the aromatic hydrocarbon stock. These fractions contain ethylbenzene of the same number of carbons in addition to the xylene isomers. Very good results can be obtained in this catalyst composition when using a $C_8$-aromatic hydrocarbon fraction which contains the xylene isomers and ethylbenzene in a total amount of at least 80%, preferably at least 90% by weight, based on the weight of the fraction.

Isomerization of the aromatic hydrocarbon stock can be performed under known reaction conditions except that the above-specified catalyst is used. The reaction temperature is generally 250° to 450° C., preferably 270° to 400° C., especially preferably 280° to 380° C., and the partial pressure of hydrogen is generally 0 to 25 kg/cm$^2$.G, preferably 0 to 20 kg/cm$^2$.G, especially preferably 0 to 12 kg/cm$^2$.G.

In practice, the starting aromatic hydrocarbon stock is fed at a rate which can be varied widely according to the type of the hydrocarbon stock used, the type of the catalyst, etc. It is generally advantageous to feed the hydrocarbon stock at a weight hourly space velocity of about 1 to about 500, preferably 2 to 100, more preferably 3 to 50.

Not only can the catalyst composition of the invention be used advantageously in the isomerization reaction of xylenes, but also it can be utilized in the transalkylation and dealkylation (particularly selective dealkylation of an alkyl group having at least 2 carbon atoms) of alkyl aromatic hydrocarbons and the alkylation of aromatic hydrocarbons.

The catalyst composition of this invention also becomes an excellent catalyst having high activity and a long active lifetime in the reforming of naphtha involving dehydrogenation of naphthenes, isomerization and cracking of n-paraffins, and dehydrogenation and cyclization of paraffins.

In the present specification and appended claims, the "weight hourly space velocity" is a value calculated in accordance with the following equation.

$$\frac{\text{Weight of the starting hydrocarbon stock fed per hour}}{\text{Weight of the catalyst}}$$

The "weight of the catalyst", as used herein, denotes the weight of crystalline aluminosilicate which forms the base of the catalyst.

The isomerization reaction is carried out in the presence of hydrogen. The rate of feeding hydrogen in this case can be varied widely according to the type of the aromatic hydrocarbon material and/or the catalyst, etc. Generally, it is appropriate to feed hydrogen at such a rate that the hydrogen/hydrocarbon mole ratio is generally from 0.1 to 15, preferably 1 to 10, more preferably from 1 to 8.

The catalyst composition of this invention brings about the following excellent technical advantages over similar conventional techniques, and can contribute greatly to industry.

(1) Since the hydrogenation and the demethylation of xylene can be markedly inhibited, a loss of xylene is decreased drastically, and the isomerization yield of xylene increases.

(2) Since the process can be operated under an elevated hydrogen partial pressure, the efficiency of the xylene manufacturing facilities can be greatly increased.

(3) Coke formation on a catalyst can be inhibited, and the operating efficiency of the apparatus can be improved greatly.

The following Examples illustrate the present invention in greater detail.

EXAMPLE 1

(a) Preparation of H-ZSM-5

Zeolite ZSM-5 was synthesized in accordance with the method disclosed in the specification of U.S. Pat. No. 3,965,207. In the synthesis, n-tripropylamine and n-propyl bromide were added as a source of an organic nitrogen cation. The synthesized product was identified as ZSM-5 from its X-ray diffraction pattern. The resulting ZSM-5 was filtered, and fully washed with water. It was dried in a drying oven at 100° C. for 8 hours, and then at 200° C. for 16 hours, and then calcined in an electric muffle furnace under an air stream at 450° C. for 16 hours. Then, 250 g of the calcined product was subjected to ion-exchange at 80° C. for 24 hours using 1.5 liters of a 5% by weight aqueous solution of ammonium chloride. Further this procedure was repeated two times. Then, the product was thoroughly washed with water, dried in a drying oven at 100° C. for 8 hours and 200° C. for 16 hours, and in an electric muffle furnace under a stream of air at 450° C. for 16 hours to obtain $H^{30}$-form zeolite ZSM-5 which contained 0.05% by weight of sodium and had a silica/alumina mole ratio of 92.

(b) Preparation of Pt/ZSM-5

0.173 g of $[Pt(NH_3)_4]Cl_2$ was dissolved in 90 cc of water, and 30 g of the $H^+$-form ZSM-5 obtained by the method shown in (a) above was added. With occasional shaking, the zeolite was immersed therein at 50° C. for 8 hours, then filtered, washed fully with water at room temperature, and dried in an drying oven at 100° C. for 8 hours and then at 200° C. for 16 hours. It was calcined in an electric muffle furnace under a stream of air at 450° C. for 3 hours to afford Pt/ZSM-5 which contained 0.24%, based on the total weight of the catalyst, of platinum (this catalyst is referred to as catalyst A).

(c) Preparation of Pt/ZSM-5

120 ml of 2.5% aqueous ammonia was added to 22.0 g of H-ZSM-5, and while they were sufficiently stirred with a glass rod, a solution of 0.113 g of $[Pt(NH_3)_4]Cl_2$ in 60 ml of a 2.5% aqueous ammonia was added dropwise by a pipette. The mixture was stirred at room temperature for 5 hours using a magnetic stirrer, and then washed with deionized water until the electric conductivity of the filtrate became not more than 15 $\mu v/cm$. The product was then dried at 100° C. and 200° C. both for 4 hours, and calcined in an electric muffle furnace under a stream of air for 4 hours. The platinum content of the product was 0.28% by weight. The product is referred to as catalyst B. By a similar operation, catalyst C to H having the platinum contents shown in Table 1 were prepared.

(d) Pt-ZSM-5 with various metals supported thereon

Each of the various metal salts shown in Table 1 was weighed so that the atomic ratio of the metal to platinum reached the prescribed values shown in Table 1, and dissolved in a suitable solvent (deionized water unless otherwise specified). To the solution was added Pt-ZSM-5 prepared as above, and the mixture was evaporated to dryness to impregnate the metal salt therein. The product was dried at 100° C. and then at 200° C., and calcined in an electric muffle furnace under a stream of air at 450° C. to prepare powders of Pt-ZSM-5 having various metals supported thereon.

As a specific example, Pt-ZSM-5 having indium supported thereon was prepared as follows:

13.5 mg of $InCl_3 \cdot 4H_2O$ (the atomic ratio of indium to platinum corresponded to 1.2) was dissolved in 50 ml of deionized water, and 3 g of catalyst E was added. In a constant temperature bath at 70° C., the mixture was heated for 4 hours with occasional shaking. Then, using a rotary evaporator, water was distilled off at a temperature of 45° C. The solid residue was dried in a drying oven at 100° C. and 200° C. both for 4 hours, and calcined in an electric muffle furnace under a stream of nitrogen at 450° C. for 4 hours to afford a catalyst E-1.

TABLE 1

| Catalyst series No. | Concentration of platinum (wt. %, based on zeolite) | Metal (b) | Atomic ratio of metal (b) to Pt | Salt of metal (b) | Solvent |
|---|---|---|---|---|---|
| A | 0.24 | — | — | — | — |
| A-1 | " | Germanium | 0.9 | $GeCl_4$ | Isopropyl alcohol |
| A-2 | " | Tin | 0.5 | $SnCl_2 \cdot 2H_2O$ | HCl/water |
| A-3 | " | Lead | 0.3 | $Pb(NO_3)_2$ | Water |
| A-4 | " | Chromium | 1.3 | $Cr(NO_3)_3 \cdot 9H_2O$ | " |
| A-5 | " | Molybdenum | 0.7 | $(NH_4)_6Mo_7O_{27} \cdot 4H_2O$ | " |
| A-6 | " | Tungsten | 0.4 | $(NH_4)_{10}W_{12}O_{41} \cdot 5H_2O$ | " |
| A-7 | " | Osmium | 0.3 | $OsO_4$ | " |
| A-8 | " | Palladium | 0.6 | $Pd(NH_3)_4Cl_2$ | " |
| B | 0.27 | — | — | — | — |
| B-1 | " | Strontium | 0.5 | $Sr(ClO_4)_2 \cdot 2H_2O$ | Water |
| B-2 | " | Beryllium | 0.5 | $Be(NO_3)_2 \cdot 3H_2O$ | " |
| B-3 | " | Gallium | 0.5 | $Ga(NO_3)_2 \cdot 8H_2O$ | " |
| B-4 | " | Cerium | 0.5 | $Ce(NO_3)_3 \cdot 6H_2O$ | " |
| B-5 | " | Barium | 0.2 | $Ba(NO_2)_2 \cdot H_2O$ | " |
| C | 0.28 | — | — | — | — |
| C-1 | " | Yttrium | 1.1 | $Y(NO_3)_3 \cdot 6H_2O$ | Water |
| C-2 | " | Zirconium | 0.5 | $Zr(NO_3)_2 \cdot 2H_2O$ | " |
| D | 0.27 | — | — | — | — |
| D-1 | " | Zinc | 1.1 | $Zn(NO_3)_2 \cdot 6H_2O$ | Water |
| D-2 | " | Titanium | 0.5 | $Ti(SO_4)_2$ | " |
| E | 0.26 | — | — | — | — |
| E-1 | " | Indium | 1.2 | $InCl_3 \cdot 4H_2O$ | Water |
| E-2 | " | Lanthanum | 1.2 | $La(NO_3)_3 \cdot 6H_2O$ | " |

TABLE 1-continued

| Catalyst series No. | Concentration of platinum (wt. %, based on zeolite) | Metal (b) | Atomic ratio of metal (b) to Pt | Salt of metal (b) | Solvent |
|---|---|---|---|---|---|
| F | 0.27 | — | — | — | — |
| F-1 | " | Cadmium | 1.1 | $CdCl_2.2\frac{1}{2}H_2O$ | Water |
| G | 0.25 | — | — | — | — |
| G-1 | " | Mercury | 1.2 | $Hg(NO_3)_2.H_2O$ | Water |
| H-1 | 0.5 | Tin | 0.3 | $SnCl_2.2H_2O$ | HCl/Water |
| H-2 | " | Tin | 3.3 | $SnCl_2.2H_2O$ | " |

EXAMPLE 2

The powdery catalysts HZSM-5, Pt/ZSM-5 and bimetallic ZSM-5 obtained in Example 1 were each molded into a size of 10 to 20 mesh. Each of the molded articles was calcined in an electric muffle furnace in air at 450° C. for 8 hours, and then 1.5 ml of the calcined molded catalyst was packed into a Pyrex glass tube reactor. Nitrogen gas was passed through n-hexane at 25° C. in an gas absorbing bottle, and the saturated gaseous stream (the partial pressure of hexane was 0.2 atm.) was fed into the catalyst bed at a rate of 10 ml/min. The reaction temperature was adjusted such that the conversion of n-hexane was maintained at 5 to 40%. The above conversion could be achieved at a reaction temperature of 150° to 250° C.

The conversion of n-hexane is defined as follows:

$$\text{Conversion of n-hexane } (\epsilon) = \frac{\text{Concentration of n-hexane (\% by weight) in the product}}{100}$$

The product formed during a time period between 20 minutes and 30 minutes after the start of feeding was sampled, and analyzed by gas chromatography.

The reaction velocity constant at each reaction temperature was calculated as follows.

$$k = (1/\tau)\ln\frac{1}{1-\epsilon}$$

wherein k (sec$^{-1}$) is the rate constant, $\tau$ (sec) is the volume (ml) of the catalyst/the flow rate (ml/sec) of the feed gas, and $\epsilon$ is the conversion of n-hexane.

The reaction rate constant of the catalyst at 200° C. can be determined from the Arrhenius' plot.

As a standard silica-alumina catalyst, N-631-HN (product of Nikki Chenicals Ltd.) was used, and its reaction rate constant was calculated by the same procedure as above. An n-hexane conversion of 5 to 40% was obtained at a temperature of 400° to 500° C. The reaction velocity constant of the standard catalyst at 200° C. was calculated by an extrapolation method using the activation energy obtained within the above-mentioned temperature range.

The ratio of the reaction rate constant of the catalyst to that of the standard catalyst at 200° C. is defined as the activity index (A.I.). The A.I. values of H-ZSM-5 and A-G series catalysts are summarized in Table 2.

It is seen from Table 2 that the ZSM-5 containing Pt (a) and the metal (b) has sufficient catalytic activity.

TABLE 2

| Catalyst | Metal (b) | A.I. |
|---|---|---|
| H—ZSM-5 | — | 16,000 |
| A | — | 11,000 |
| A-1 | Ge | 8,800 |
| A-2 | Sn | 8,700 |
| A-3 | Pb | 7,700 |
| A-4 | Cr | 7,500 |
| A-5 | Mo | 7,900 |
| A-6 | W | 9,900 |
| A-7 | Os | 9,500 |
| A-8 | Pd | 9,900 |
| B | — | 11,000 |
| B-1 | Sr | 7,700 |
| B-2 | Be | 8,700 |
| B-3 | Ga | 7,900 |
| B-4 | Ce | 10,000 |
| B-5 | Ba | 4,800 |
| C | — | 11,000 |
| C-1 | Y | 9,500 |
| C-2 | Zr | 10,000 |
| D | — | 11,000 |
| D-1 | Zn | 7,100 |
| D-2 | Ti | 3,400 |
| E | — | 11,000 |
| E-1 | In | 9,700 |
| E-2 | La | 8,800 |
| F | — | 11,000 |
| F-1 | Cd | 6,000 |
| G | — | 11,000 |
| G-1 | Hg | 4,100 |

EXAMPLE 3

To remove the adhering water, the powdery H-ZSM-5, Pt/ZSM-5 and bimetallic ZSM-5 catalysts obtained in Example 1 were each calcined in an electrical muffle furnace in air at 450° C. for 8 hours. About 1 g of each of the calcined catalysts was weighed into a weighing bottle. The weighed zeolite was then allowed to stand in a desiccator containing an adsorbent solvent for 6 hours at 25° C. and 120±20 mmHg to allow adsorption to saturation. Then, the solvent was removed from the desiccator, and the zeolite was evacuated at 25° C. and 120±20 mmHg for 2 hours. The zeolite was again weighed. The amount of the material adsorbed to zeolite is calculated from the following equation.

$$v = \frac{W_2 - W_1}{W_1}$$

wherein v is the amount of the material adsorbed per unit weight of the zeolite, and $W_1$ and $W_2$ are the weights of the zeolite before and after adsorption, respectively.

By the above method, the n-hexane/cyclohexane sorption rate was calculated, and the results are shown in Table 3.

It is seen from Table 3 that the ZSM-5 containing Pt (a) and the metal (b) has favorable adsorption selectivity. This brings about the important advantage that its selectivity for a catalytic reaction is increased.

TABLE 3

| Catalyst | Metal (b) | $\left(\dfrac{\text{Cyclohexane}}{\text{n-hexane}}\right)$ soroption ratio |
|---|---|---|
| H—ZSM-5 | — | 0.60 |
| A | — | 0.46 |
| A-1 | Ge | 0.44 |
| A-2 | Sn | 0.40 |
| A-3 | Pb | 0.42 |
| A-4 | Cr | 0.45 |
| A-5 | Mo | 0.49 |
| A-6 | W | 0.35 |
| A-7 | Os | 0.41 |
| A-8 | Pd | 0.40 |
| B | — | 0.46 |
| B-1 | Sr | 0.37 |
| B-2 | Be | 0.51 |
| B-3 | Ga | 0.46 |
| B-4 | Ce | 0.37 |
| B-5 | Ba | 0.45 |
| C | — | 0.46 |
| C-1 | Y | 0.44 |
| C-2 | Zr | 0.37 |
| D | — | 0.46 |
| D-1 | Zn | 0.48 |
| D-2 | Ti | 0.46 |
| E | — | 0.46 |
| E-1 | In | 0.49 |
| E-2 | La | 0.44 |
| F | — | 0.46 |
| F-1 | Cd | 0.47 |
| G | — | 0.46 |
| G-1 | Hg | 0.44 |

EXAMPLE 4

Each of the powdery catalysts Pt/ZSM-5 and bimetallic ZSM-5 obtained in Example 1 was mixed fully with chromatographic alumina gel (300 mesh) in a weight ratio of 1:1, and the mixture was then molded to a size of 10 to 20 mesh. The molded article was calcined in an electrical muffle furnace in air at 450° C. for 8 hours. About 4 g of the molded article, and packed into a fixed bed reactor. The calcined catalyst was then reduced in hydrogen gas at 400° C. for 2 hours, and then benzene was fed at a rate of 16 g/hour together with hydrogen gas. The reaction conditions were as follows:

Reaction temperature: 200° C.
WHSV: 8.0 hr$^{-1}$ (based on the weight of the zeolite)
Hydrogen/benzene mole ratio: 1:1
Pressure: atmospheric pressure
Purity of benzene: 99.98%

After a lapse of two hours from the initiation of feeding, the product was sampled and analyzed by gas chromatography. The total weight percent of $C_6$ naphthenes was measured, and defined as H.I.

Table 4 summarizes the hydrogenation index (H.I.) of A-H series catalysts.

It is seen from Table 4 that the metal (b) markedly reduces the hydrogenating activity of the catalyst on the benzene ring.

TABLE 4

| Catalyst | Metal (b) | H. I. |
|---|---|---|
| A | — | 10.90 |
| A-1 | Ge | 1.98 |
| A-2 | Sn | 0.45 |
| A-3 | Pb | 4.89 |
| A-4 | Cr | 2.59 |
| A-5 | Mo | 2.88 |
| A-6 | W | 5.23 |
| A-7 | Os | 4.09 |
| A-8 | Pd | 4.04 |
| B | — | 7.92 |
| B-1 | Sr | 2.80 |
| B-2 | Be | 4.26 |
| B-3 | Ga | 2.20 |
| B-4 | Ce | 4.40 |
| B-5 | Ba | 0.35 |
| C | — | 1.05 |
| C-1 | Y | 0.74 |
| C-2 | Zr | 0.65 |
| D | — | 3.37 |
| D-1 | Zn | 2.46 |
| D-2 | Ti | 0.24 |
| E | — | 4.86 |
| E-1 | In | 0.11 |
| E-2 | La | 1.46 |
| F | — | 5.90 |
| F-1 | Cd | 0.05 |
| G | — | 5.55 |
| G-1 | Hg | 0.79 |

EXAMPLE 5

Chromatographic alumina gel (300 mesh) was added to each of the powdery catalysts A and A-2 obtained in Example 1 in a weight ratio of 1:1. They were well mixed and molded into a size of 10 to 20 mesh. Each of the molded products was calcined in an electric muffle furnace under a stream of air at 450° C. for 8 hours, and filled in a fixed bed reactor. Then, each of the molded catalysts was reduced in a stream of hydrogen at 400° C. for 2 hours, and subsequently, a xylene isomeric mixture having the composition shown in Table 2 was fed to the reactor.

The reaction conditions were as follows:
Temperature: 350° C.
Weight hourly space velocity (WHSV): 8.0 hr$^{-1}$ (based on the weight of zeolite)
Hydrogen/aromatic hydrocarbon mole ratio: 3:1
Pressure: 7.4 kg/cm$^2$.G The composition of the product after a lapse of 50 hours from the initiation of feeding was as shown in Table 5.

It is seen from the results obtained that when tin is added as the metal (b) to Pt/ZSM-5, the approach to equilibrium of PX, which shows the degree of isomerization activity, does not at all decrease, and that while the degree of deethylation inherent to platinum is maintained at a high level, the inherent ability of platinum to hydrogenate the benzene ring and demethylate the xylenes can be drastically inhibited. Thus, a loss of xylene can be greatly decreased.

TABLE 5

| | | Product | |
|---|---|---|---|
| | | Catalyst A-2 (Pt/Sn) | Catalyst A Pt |
| Composition (wt. %) | Feed stock | | |
| $C_2$–$C_4$ ⎫ (*) | — | 1.38 | 2.54 |
| $C_5$–$C_9$ ⎭ | 0.02 | 0.12 | 5.52 |
| Benzene | — | 4.11 | 5.10 |
| Toluene | 2.01 | 3.08 | 5.12 |
| Ethylbenzene | 14.85 | 8.22 | 5.79 |
| p-Xylene | 9.18 | 19.49 | 17.62 |
| m-Xylene | 56.45 | 44.49 | 40.22 |
| o-Xylene | 17.44 | 17.76 | 16.05 |
| $C_9$ aromatics | 0.05 | 0.70 | 1.71 |
| $C_{10}^+$ aromatics | — | 0.22 | 0.33 |
| PX approach to equilirium (%) | | 101.0 | 101.1 |
| FB composition ratio (%) | | 44.6 | 61.0 |
| Xylene loss (%) | | 1.54 | 11.0 |

TABLE 5-continued

|  | Product | |
|---|---|---|
|  | Catalyst A-2 (Pt/Sn) | Catalyst A Pt |
| $E_B$ decomposition ratio/xylene loss | 29.0 | 5.5 |
| Deethylation ratio (%) | 79.0 | 88.5 |
| Amount of demethylaction (mmole) | 6.63 | 19.55 |
| Amount of $C_6^+$ naphthenes formed (wt. %) | 0.06 | 4.24 |
| $C_6$ naphthenes/benzene (wt. %) | 0.20 | 14.01 |

NA: non-aromatics composed mainly of paraffins and naphthenes.

The various items given in the above and subsequent tables are defined as follows:

$$PX \text{ approach to equilibrium (\%)} = \frac{[PX]_P - [PX]_F}{[PX]_E - [PX]_F} \times 100$$

$$EB \text{ decomposition ratio (\%)} = \frac{[EB]_F - [EB]_P}{[EB]_F} \times 100$$

$$\text{Xylene loss (\%)} = \frac{[X]_F - [X]_P}{[X]_F} \times 100$$

Deethylation ratio (%) =

$$\frac{\left(\begin{array}{c}\text{Total moles}\\\text{of } EB \text{ consumed}\end{array}\right) - \left(\begin{array}{c}\text{Moles of } EB\\\text{consumed by dis-}\\\text{proportionation and}\\\text{transalkylation}\end{array}\right)}{\text{Total moles of } EB \text{ consumed}}$$

Amount of demethylation =

$$\left(\begin{array}{c}\text{Sum of the moles}\\\text{of toluene and } C_7\\\text{naphthene formed}\end{array}\right) - \left(\begin{array}{c}\text{Moles of } C_9\\\text{aromatic formed}\end{array}\right)$$

$$\text{Ring loss ratio (\%)} = \left(1 - \frac{\text{Moles of the benzene ring in the product}}{\text{Moles of the benzene ring in the feed}}\right) \times 100$$

The various abbreviations given above mean the following.

$[PX]_F$: The concentration (% by weight) of p-xylene in the three xylene isomers in the feed stock.

$[PX]_P$: The concentration (% by weight) of p-xylene in the three xylene isomers in the product.

$[PX]_E$: The equilibrium concentration (% by weight) of p-xylene in the xylene isomers at the reaction temperature.

$[EB]_F$: The concentration (% by weight) of EB in the feed stock.

$[EB]_P$: The concentration (% by weight) of EB in the product.

$[X]_F$: The concentration (% by weight) of the three xylene mixt isomers in the feed stock.

$[X]_P$: The concentration (% by weight) of the three xylene isomers in the product.

EXAMPLE 6

The powdery catalysts B-5, D-2, E, E-1 and F-1 obtained in Example 1 were molded, calcined and reduced in the same way as in the catalysts A and A-2 described in Example 5, and used in the isomerization of xylene under the same reaction conditions in the same reactor using the same starting material as in Example 5. The various data obtained after a lapse of 70 hours from the initiation of feeding were as shown in Table 6. The definitions of these data are the same as in Example 5.

It is seen as in Example 5 that when Ba, In, Ti and Cd were added, (1) the isomerization activity and the deethylation activity of Pt are not degraded, and (2) the activity of hydrogenating the benzene ring and demethylating xylenes is inhibited.

TABLE 6

|  | Catalyst | | | | |
|---|---|---|---|---|---|
|  | E (Pt) | B-5 (Pt, Ba) | E-1 (Pt, In) | D-2 (Pt, Ti) | F-1 (Pt, Cd) |
| PX approach to equilibrium (%) | 100.9 | 102.0 | 103.0 | 101.6 | 102.3 |
| EB decomposition ratio (%) | 60.2 | 52.3 | 50.5 | 46.2 | 52.0 |
| Xylene loss (%) | 5.59 | 3.93 | 1.53 | 1.23 | 1.32 |
| EB decomposition ratio/xylene loss | 10.8 | 13.3 | 33.0 | 37.6 | 39.4 |
| Deethylation ratio (%) | 91.4 | 80.8 | 83.6 | 87.6 | 85.2 |
| Amount of demethylation (mmol) | 7.32 | 10.22 | 5.43 | 5.55 | 3.88 |
| Amount of $C_6 +$ naphthenes formed (wt. %) | 3.18 | 0.54 | 0.08 | 0.39 | 0.05 |
| $C_6$ naphthenes/benzene (wt. %) | 21.40 | 3.09 | 0.59 | 3.34 | 0.27 |

EXAMPLE 7

Benzene was hydrogenated in a fixed bed reactor using the same catalysts A, A-2, B-5, D-2, E, E-1 and F-1 as described in Examples 5 and 6. The reaction conditions were as follows:

Temperature: 200° C.
Weight hourly space velocity: 8.0 hr$^{-1}$ (based on the weight of zeolite)
Hydrogen/benzene mole ratio: 1:1
Pressure: atmospheric pressure
Feed stock: 99.98 wt. % benzene The conversion of benzene in 2 hours after the initiation of feeding is shown in Table 7.

FIG. 1 of the accompanying drawings shows the relation between the amount of liquid non-aromatics (at least 99 wt. % of which consisted of $C_6$ naphthenes) formed by the hydrogenation of benzene under the aforesaid reaction conditions at atmospheric pressure and the amount of the hydrogenation products ($C_6^+$ naphthenes) of xylenes obtained in the isomerization of xylenes under the reaction conditions at elevated pressure described in Examples 5 and 6. A positive correlation is seen between the two. This shows that the metal (b) which inhibits the formation of naphthenes during the isomerization of xylenes under elevated pressure inhibits the hydrogenation of benzene at atmospheric pressure.

TABLE 7

| Catalyst | Type of metal (b) | Non-aromatics in the product (wt. %) |
|---|---|---|
| A | None | 10.90 |
| E | None | 4.86 |
| A-2 | Sn | 0.45 |
| B-5 | Ba | 0.25 |
| D-2 | Ti | 0.24 |
| E-1 | In | 0.11 |

TABLE 7-continued

| Catalyst | Type of metal (b) | Non-aromatics in the product (wt. %) |
|---|---|---|
| F-1 | Cd | 0.05 |

Non-aromatics in the product: only liquid non-aromatics without gaseous non-aromatics.

EXAMPLE 8

The powdery catalysts described in Table 8 which were obtained in Example 1 were molded, and calcined in the same way as in Example 5. In an fixed bed reactor, the same benzene as used in Example 7 was hydrogenated under the same reaction conditions as shown in Example 7. The results are shown in Table 8.

As in seen from Table 8, the addition of the metals (b) leads to the inhibition of the activity of hydrogenating the benzene ring. It is clear from FIG. 1 that the amount of $C_6^+$ naphthenes in the xylene isomerization products decreases, and the loss of xylenes can be reduced.

TABLE 8

| Catalyst | Type of metal (b) | Liquid non-aromatics in products (wt. %) |
|---|---|---|
| A | None | 10.90 |
| A-1 | Ge | 1.98 |
| A-3 | Pb | 4.89 |
| A-4 | Cr | 2.59 |
| A-5 | Mo | 2.88 |
| A-6 | W | 5.23 |
| A-7 | Os | 4.09 |
| A-8 | Pd | 4.04 |
| B | None | 7.92 |
| B-1 | Sr | 2.80 |
| B-2 | Br | 4.26 |
| B-3 | Ga | 2.20 |
| B-4 | Ce | 4.40 |
| C | None | 1.05 |
| C-1 | Y | 0.74 |
| C-2 | Zr | 0.65 |
| D | None | 3.37 |
| D-1 | Zn | 2.46 |
| E | None | 4.86 |
| E-2 | La | 1.46 |
| G | None | 5.55 |
| G-1 | Hg | 0.79 |

EXAMPLE 9

Xylenes were isomerized at atmospheric pressure using the catalysts as used in Example 8.

The catalysts were calcined and reduced in the same way as described in Example 8. The reaction conditions were a temperature of 380° C. and a WHSV of 6 for the catalysts B and B-1, and a temperature of 350° C. and a WHSV of 8 for the other catalysts. The other reaction conditions were the same as in Example 8, and the feed stock was the same as that used in Example 5.

After a lapse of 20 hours from the initiation of the feeding, the characteristic values of the reaction defined in Example 5 were as shown in Table 9.

It is seen from Table 9 that when the metals (b) shown in Table 9 are added to the platinum-ZSM-5 catalyst, the following effects can be obtained.

(1) The ability of the catalyst to isomerize xylenes is retained almost completely.

(2) The ability of deethylating ethylbenzene, which is inherent to platinum, is not degraded.

(3) The activity of platinum itself to demethylate xylene is inhibited.

Taken together with the fact shown in Example 8, it is evident that by adding the metals (b) shown in Table 9 (the same as those shown in Table 8) to the Pt-ZSM-5 catalyst, there can be obtained catalysts for isomerization of xylenes, which greatly reduce the loss of xylenes.

TABLE 9

| Catalyst | Metal (b) | PX approach to equilibrium (%) | EB decomposition ratio (A) (%) | Xylene loss (B) (%) | A/B | Deethylation ratio (%) | Demethylation ratio (%) |
|---|---|---|---|---|---|---|---|
| A | None | 98.8 | 51.6 | 1.45 | 35.6 | 94.1 | 64.9 |
| A-1 | Ge | 99.8 | 52.5 | 0.98 | 53.6 | 93.9 | 46.2 |
| A-3 | Pb | 98.9 | 40.5 | 0.52 | 77.9 | 90.8 | 18.5 |
| A-4 | Cr | 98.4 | 41.9 | 0.56 | 74.8 | 91.6 | 32.4 |
| A-5 | Mo | 99.2 | 39.1 | 0.55 | 71.1 | 88.5 | 23.2 |
| A-6 | W | 99.7 | 42.5 | 0.58 | 73.3 | 90.9 | 26.3 |
| A-7 | Os | 99.5 | 49.0 | 0.83 | 59.8 | 94.0 | 44.8 |
| A-8 | Pd | 100.3 | 48.0 | 1.12 | 42.9 | 93.5 | 62.5 |
| B | None | 100.8 | 90.0 | 4.77 | 18.9 | 98.7 | 62.3 |
| B-1 | Sr | 101.0 | 80.2 | 2.58 | 31.1 | 98.7 | 58.1 |
| B-2 | Be | 101.3 | 43.0 | 0.84 | 51.2 | 90.4 | 40.7 |
| B-3 | Ga | 100.8 | 32.7 | 0.53 | 61.7 | 90.7 | 13.4 |
| B-4 | Ce | 100.9 | 51.6 | 0.98 | 52.7 | 93.9 | 41.5 |
| C | None | 100.9 | 46.8 | 0.86 | 54.4 | 91.9 | 37.0 |
| C-1 | Y | 100.9 | 48.6 | 0.71 | 53.4 | 91.8 | 38.3 |
| C-2 | Zr | 101.1 | 51.0 | 1.00 | 51.0 | 92.7 | 38.4 |
| D | None | 100.9 | 45.6 | 0.86 | 53.0 | 93.1 | 42.9 |
| D-1 | Zn | 100.1 | 35.4 | 0.48 | 73.8 | 88.0 | 29.1 |
| E | None | 98.4 | 46.3 | 0.87 | 53.2 | 93.3 | 66.0 |
| E-2 | La | 99.5 | 43.1 | 1.22 | 35.3 | 85.9 | 33.6 |
| G | None | 97.3 | 43.2 | 0.62 | 69.7 | 91.3 | 53.3 |
| G-1 | Hg | 94.5 | 40.8 | 0.60 | 68.0 | 89.4 | 51.0 |

EXAMPLE 10

Chromatographic alumina gel (300 mesh) was added to each of the powdery catalysts H-1 and H-2 obtained in Example 1 in a weight ratio of 1:1. They were fully mixed and molded into a product having a size of 10 to 20 mesh. The molded product was calcined in air at 450° C. for 8 hours, and subsequently, reduced in a stream of hydrogen at 400° C. for 2 hours.

Benzene was hydrogenated using the resulting catalyst by the same method and under the same conditions as described in Example 7. The conversion for benzene in 2 hours after initiation of feeding was as shown in Table 10. Subsequently, xylenes were isomerized by the same method and under the same conditions as described in Example 9. The characteristic values of the reaction after a lapse of 5 hours from the initiation of feeding were as shown in Table 11. The definitions of the characteristic values of the reaction were the same as those given in Example 5.

It is seen from Table 11 that when the Sn/Pt atomic ratio is too low, the effect of inhibiting the activity of hydrogenating the benzene ring is insufficient, and on the other hand, if it is too high, the activities of isomerizing xylenes and decomposing ethylbenzene decrease.

TABLE 10

| Catalyst | H-1 | H-2 |
| --- | --- | --- |
| Sn/Pt atomic ratio | 0.33 | 3.3 |
| Conversion of benzene (%) | 14.1 | 0.3 |

TABLE 11

| Catalyst | H-1 | H-2 |
| --- | --- | --- |
| PX approach to equilibrium (%) | 99.2 | 90.5 |
| EB decomposition ratio (%) | 45.5 | 34.5 |
| Xylene loss (%) | 0.58 | 0.31 |
| Deethylation ratio (%) | 91.1 | 85.8 |
| Demethylation ratio (%) | 29.0 | — |

What we claim is:

1. A catalyst composition comprising
   (i) a crystalline aluminosilicate selected from the group consisting of zeolite ZSM-5, zeolite ZSM-11, zeolite ZSM-12, zeolite ZSM-35 and zeolite ZSM-38 and having a silica/alumina mole ratio of 20 to 1,000; and
   (ii) at least two metals which are
   (a) platinum and
   (b) at least one other metal selected from the group consisting of titanium, barium, and lanthanum.

2. The composition of claim 1 wherein the amount of platinum is 0.001 to 2% by weight based on the weight of the aluminosilicate.

3. The composition of claim 2 wherein the amount of platinum is 0.005 to 1.5% by weight based on the weight of the aluminosilicate.

4. The composition of claim 1 wherein the atomic ratio of platinum to the other metal (b) is in the range of from 1:0.01 to 1:10.

5. The composition of claim 4 wherein the atomic ratio of platinum to the other metal (b) is in the range of from 1:0.05 to 1:5.

6. The composition of claim 1 wherein the aluminosilicate has a silica/alumina ratio of from 30 to 200.

7. The composition of claim 1 wherein the aluminosilicate is zeolite ZSM-5.

8. The composition of claim 1 which has a cyclohexane/n-hexane sorption ratio of not more than 0.95.

9. The composition of claim 8 which has a cyclohexane/n-hexane sorption ratio of not more than 0.8.

10. The composition of claim 1 which has an activity index of not less than 100.

11. The composition of claim 10 which has an activity index of not less than 100.

12. The composition of claim 1 which has a hydrogenation index of not more than 6%.

13. The composition of claim 12 which has a hydrogenation index of not more than 2%.

14. The composition of claim 1 which further comprises a refractory inorganic oxide as a binder.

15. The composition of claim 14 wherein the amount of the refractory inorganic oxide is 1 to 99% by weight based on the weight of the composition.

16. The composition of claim 1 which is in the form of pellets or tablets.

17. The composition of claim 2 wherein the atomic ratio of platinum to the other metal (b) is in the range of from 1:01 to 1:10.

18. The composition of claim 1 wherein the other metal (b) is titanium.

19. The composition of claim 1 wherein the other metal (b) is barium.

20. The composition of claim 1 wherein the other metal (b) is lanthanum.

* * * * *